(12) United States Patent
Turner et al.

(10) Patent No.: US 10,463,433 B2
(45) Date of Patent: Nov. 5, 2019

(54) SYSTEMS AND METHODS FOR SPINAL CORRECTION SURGICAL PLANNING

(71) Applicant: NUVASIVE, INC., San Diego, CA (US)

(72) Inventors: Alex Turner, San Diego, CA (US); Jeffrey Harris, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 15/448,119

(22) Filed: Mar. 2, 2017

(65) Prior Publication Data
US 2017/0252107 A1 Sep. 7, 2017

Related U.S. Application Data

(60) Provisional application No. 62/302,725, filed on Mar. 2, 2016.

(51) Int. Cl.
| | |
|---|---|
| *A61B 34/10* | (2016.01) |
| *G06N 5/04* | (2006.01) |
| *G16H 50/50* | (2018.01) |

(52) U.S. Cl.
CPC ............... *A61B 34/10* (2016.02); *G06N 5/04* (2013.01); *G16H 50/50* (2018.01); *A61B 2034/104* (2016.02); *A61B 2034/105* (2016.02); *A61B 2034/107* (2016.02)

(58) Field of Classification Search
CPC .............. A61B 34/10; A61B 2034/105; A61B 2034/107; G16H 50/50; G06N 5/04
See application file for complete search history.

(56) References Cited

U.S. PATENT DOCUMENTS

| | | | | |
|---|---|---|---|---|
| 7,346,382 B2 * | 3/2008 | McIntyre | ........... | A61N 1/36082 600/407 |
| 9,861,446 B2 * | 1/2018 | Lang | ...................... | A61B 34/10 |
| 2005/0043660 A1 * | 2/2005 | Stark | ..................... | A61F 5/0106 602/19 |
| 2007/0172797 A1 * | 7/2007 | Hada | ..................... | G09B 23/32 434/1 |

(Continued)

FOREIGN PATENT DOCUMENTS

| | | | | |
|---|---|---|---|---|
| WO | WO 2015054543 A1 * | 4/2015 | ......... | A61B 17/7083 |
| WO | WO 2015195843 A2 * | 12/2015 | ............. | A61B 34/10 |
| WO | WO 2017127838 A1 * | 7/2017 | | |

OTHER PUBLICATIONS

Farahani et al., "Prediction of the Movement Patterns for Human Squat Jumping Using the Inverse-Inverse Dynamics Technique", XIII International Symposium on Computer Simulation in Biomechanics, Jun. 30-Jul. 2, 2011, Leuven, Belgium.

*Primary Examiner* — Bitew A Dinke

(57) ABSTRACT

A system for surgical planning and assessment of spinal deformity correction is provided that has a spinal imaging system and a control unit. The spinal imaging system is configured to collect at least one digitized position of one or more vertebral bodies of a subject. The control unit is configured to receive the at least one digitized position, and calculate, based on the at least one digitized position, an optimized posture for the subject. The control unit is configured to receive one or more simulated spinal correction inputs, and based on the inputs and optimized posture, predict an optimal simulated postoperative surgical correction.

19 Claims, 12 Drawing Sheets

(56) References Cited

U.S. PATENT DOCUMENTS

| | | | |
|---|---|---|---|
| 2007/0288064 A1* | 12/2007 | Butson | A61B 5/0538 607/45 |
| 2009/0287271 A1* | 11/2009 | Blum | A61N 1/37247 607/45 |
| 2010/0191071 A1* | 7/2010 | Anderson | G06Q 10/10 600/301 |
| 2011/0054870 A1* | 3/2011 | Dariush | G06F 3/011 703/11 |
| 2012/0014580 A1* | 1/2012 | Blum | A61B 6/12 382/131 |
| 2012/0041562 A1 | 2/2012 | Shachar et al. | |
| 2012/0265268 A1* | 10/2012 | Blum | A61N 1/0553 607/46 |
| 2013/0131486 A1 | 5/2013 | Copf et al. | |
| 2013/0173240 A1 | 7/2013 | Koell et al. | |
| 2013/0218163 A1* | 8/2013 | Frey | A61B 5/0488 606/87 |
| 2013/0325069 A1* | 12/2013 | Pereiro de Lamo | A61B 17/7032 606/263 |
| 2014/0244220 A1* | 8/2014 | McKinnon | A61F 2/02 703/1 |
| 2015/0100091 A1* | 4/2015 | Tohmeh | A61B 17/7083 606/279 |
| 2016/0157751 A1* | 6/2016 | Mahfouz | A61B 5/062 600/409 |
| 2016/0235479 A1* | 8/2016 | Mosnier | A61B 17/7011 |
| 2016/0242857 A1* | 8/2016 | Scholl | A61B 17/8863 |
| 2016/0270772 A1* | 9/2016 | Beale | A61B 17/56 |
| 2017/0135770 A1* | 5/2017 | Scholl | A61B 34/20 |
| 2017/0231710 A1* | 8/2017 | Scholl | A61B 90/06 606/279 |
| 2017/0367738 A1* | 12/2017 | Scholl | A61B 34/10 |

\* cited by examiner

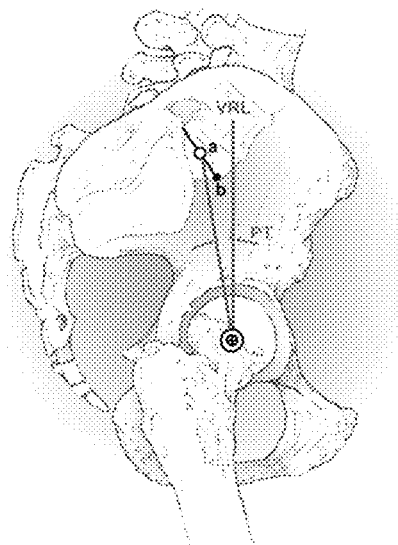 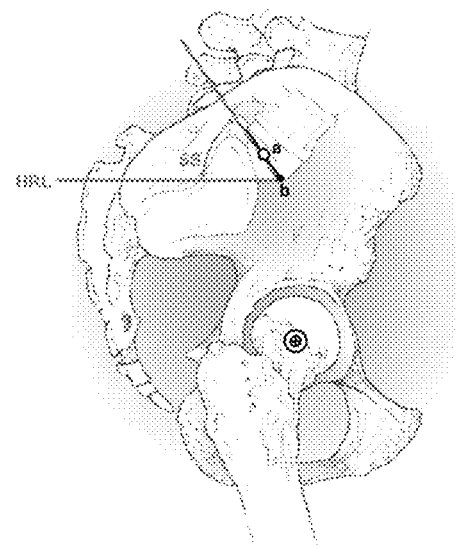
FIG. 7A　　　　　　　　　　　FIG. 7B
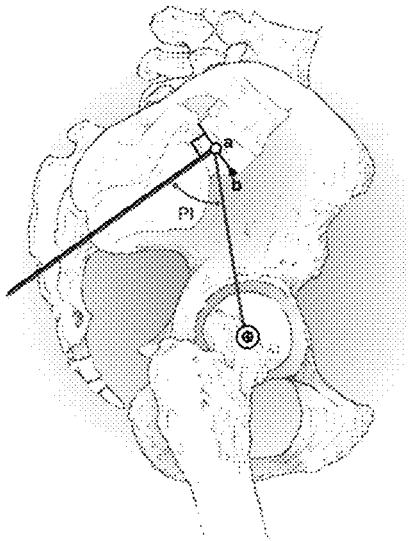
FIG. 7C

SYSTEMS AND METHODS FOR SPINAL CORRECTION SURGICAL PLANNING

CROSS REFERENCE TO RELATED APPLICATIONS

The present application claims the benefit of the priority date from U.S. Provisional Application No. 62/302,725, filed on Mar. 2, 2016, the entire contents of which are hereby expressly incorporated by reference into this disclosure as if set forth fully herein.

FIELD

The present disclosure relates generally to spinal surgery, more specifically to systems and methods relating to the planning, predicting, performing, and assessing of spinal deformity correction and compensatory changes. Such devices as well as systems and methods for use therewith are described.

BACKGROUND

The spinal column is a highly complex system of bones and connective tissues that provide support for the body and protect the delicate spinal cord and nerves. The spinal column includes a series of vertebral bodies stack atop one another, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies. The spine has a natural curvature (i.e., lordosis in the lumbar and cervical regions and kyphosis in the thoracic region) such that the end plates of the upper and lower vertebrae are enclosed toward one another.

There are many types of spinal column disorders, including scoliosis (abnormal lateral curvature of the spine), excess kyphosis (abnormal forward curvature of the spine), excess lordosis (abnormal backward curvature of the spine), spondylolisthesis (forward displacement of one vertebra over another), and other disorders caused by abnormalities, disease, or trauma (such as ruptured or slipped discs, generative disc disease, fractured vertebrae, and the like).

Patients that suffer from such conditions often experience extreme and debilitating pain, as well as diminished nerve function. Posterior fixation for spinal fusions, decompression, deformity, and other reconstructions are performed to treat these patients. The aim of posterior fixation in lumbar, thoracic, and cervical procedures is to stabilize the spinal segments, correct multi-axis alignment, and aid in optimizing the long-term health of the spinal cord and nerves.

Spinal deformity is the result of structural change to the normal alignment of the spine and is usually due to at least one unstable motion segment. The definition and scope of spinal deformity, as well as treatment options, continues to evolve. Surgical objections for spinal deformity correction include curvature correction, prevention of further deformity, improvement or preservation of neurological function, and the restoration of sagittal and coronal balance. Sagittal plane alignment and parameters in cases of adult spinal deformity (ASD) are becoming increasingly recognized as correlative to health related quality of life score (HRQOL). In literature, there are significant correlations between HRQOL scores and radiographic parameters such as Sagittal Vertical Axis (SVA), Pelvic Tilt (PT) and mismatch between pelvic incidence and lumbar lordosis.

Spinal disorders, such as degenerative processes of the human spine, loss of disc height and lumbar kyphosis, result in a reduced HRQQL. The skeleton compensates for changes in the spine caused by these disorders to maintain balance and horizontal gaze of the subject. However, such compensation requires effort and energy from the subject and is correlated to a lower HRQQL score. Current surgical planning tools do not evaluate or include compensatory changes in a subject, leading to an undercorrection of a deformity in a patient that undergoes the surgical plan and procedure. Therefore, a need continues to exist for systems and methods that include compensatory changes as part of surgical planning.

SUMMARY

The needs described above, as well as others, are addressed by embodiments of a system for spinal correction surgical planning described in this disclosure (although it is to be understood that not all needs described above will necessarily be addressed by any one embodiment), as the system for spinal correction surgical planning of the present disclosure is separable into multiple pieces and can be used in methods, such as surgical planning methods. The systems of the present disclosure may be used, for example, in a method of increasing HRQQL in a subject.

In an aspect, a system for surgical planning and assessment of spinal deformity correction in a subject is provided. The system includes a spinal imaging system capable of collecting at least one digitized position, such as on a corner, of one or more vertebral bodies of the subject. In an embodiment, digitized positions are from two or more vertebral bodies. The system includes a control unit in communication with the spinal imaging system. The control unit is configured to receive the at least one digitized position of the one or more vertebral bodies. The control unit is configured to calculate, based on the at least one digitized position, an optimized posture for the subject. The calculation of the optimized posture of a subject may include processing a parametric study. The control unit is configured to receive one or more simulated spinal correction inputs, such as sagittal alignment, muscle recruitment criteria, or surgical procedure, such as intervertebral fusion. The control unit is configured to predict a simulated postoperative surgical correction based on the received one or more simulated spinal correction inputs and the received at least one digitized position of the one or more vertebral bodies. The control unit may be configured to determine, or suggest, a surgical plan based on the predicted simulated postoperative surgical correction. The prediction of simulated postoperative surgical correction may be based on one or more values selected from the group consisting of: knee flexion, pelvic retroversion, center of mass migration, ankle flexion, spinal compensation, and a combination thereof.

In some embodiments of the system, the control unit is configured to communicate the predicted simulated postoperative spinal correction to a user. The control unit may be configured to communicate, or output, a predicted simulated postoperative surgical correction, corresponding to a variance from the calculated optimized posture. The output value of less than 0 may represent a predicted undercorrection, and the output value of greater than 0 may represent an overcorrection. The at least one digitized position of the one or more vertebral bodies may be obtained from X-ray data, computed tomography imaging data, magnetic resonance imaging data, or biplanar X-ray data from the subject. These data may be taken from a patient who is in a lateral standing position.

In an embodiment of the system, the at least one digitized position is processed by the control unit to generate a musculoskeletal model of the subject. The processing of the at least one digitized position may include inverse-inverse dynamics modeling. The musculoskeletal model may include spinopelvic parameters, ligament parameters, joint kinematics, or any combination thereof. The spinopelvic parameters may include parameters selected from the group consisting of: pelvic tilt, sacral slope, pelvic incidence, sagittal vertical axis, lumbar lordosis, thoracic kyphosis, T1 pelvic angle, and combinations thereof. The musculoskeletal model may include muscle force data or muscle activation data. The control unit may be configured to compare the generated musculoskeletal model with predetermined musculoskeletal model data levels. Data from the generated musculoskeletal model, such as muscle force data or muscle activation data, may be communicated to a user.

In some embodiments of the system, the control unit is configured to generate a sagittal curvature profile based on the received at least one digitized position of the one or more vertebral bodies. The control unit may be configured to modify the musculoskeletal model data to match the sagittal curvature profile. The musculoskeletal model data may be modified by scaling, adjusting positioning of the one or more vertebral bodies, morphing a simulated subject anatomy, or combinations thereof.

In an embodiment of the system, the simulated postoperative surgical correction includes hip compensation, knee joint compensation, or ankle joint compensation. The prediction of a simulated postoperative surgical correction may also include a prediction of trunk muscle force output and leg muscle force output. The trunk muscle force output may include an erector spinae output, multifidi output, an obliques output, semispinalis output, an abdominal muscles output, or any combination thereof. The leg muscle force output includes a soleus output, a gastrocnemius output, a hip and knee flexors output, a hip and knee extensors output, a gluteus maximus output, a gluteus minimus output, or any combination thereof.

In some embodiments of the system, the simulated postoperative surgical correction includes simulating an implant in the subject.

In another aspect, a system for surgical planning and assessment of spinal deformity correction in a subject includes a spinal imaging system capable of collecting at least one digitized position of one or more vertebral bodies of the subject. The system includes a control unit configured to receive the at least one digitized position of the one or more vertebral bodies of the subject, and calculate, based on morphing and scaling the at least one digitized position onto a model, an optimized posture for the subject.

In yet another aspect, a system for surgical planning and providing a personalized implant for a subject includes a spinal imaging system capable of collecting at least one digitized position of one or more vertebral bodies of the subject. The system includes a control unit in communication with the spinal imaging system. The control unit is configured to receive the at least one digitized position of the one or more vertebral bodies of the subject to create an initial musculoskeletal model. The control unit is configured to calculate, based on the initial musculoskeletal model, an optimized posture for the subject. The control unit is configured to generate a simulated implant to change the initial musculoskeletal model towards the calculated optimized posture; and communicate dimensional data of the simulated implant to a user. The system may further comprise a three dimension printer configured to create at least part of the simulated implant.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIGS. 7A-7C illustrate bones in a pelvic region of a subject.

DETAILED DESCRIPTION

Illustrative embodiments of a system for surgical planning and assessment of spinal deformity correction are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system for surgical planning and assessment of spinal deformity correction in a subject and related systems and methods disclosed herein boast a variety of inventive features and components that warrant patent protection, both individually and in combination.

Values given here may be approximate (i.e., +1-20%, or 10%) such as to account for differences in surgical technique and patient-specific factors.

Figure 1:
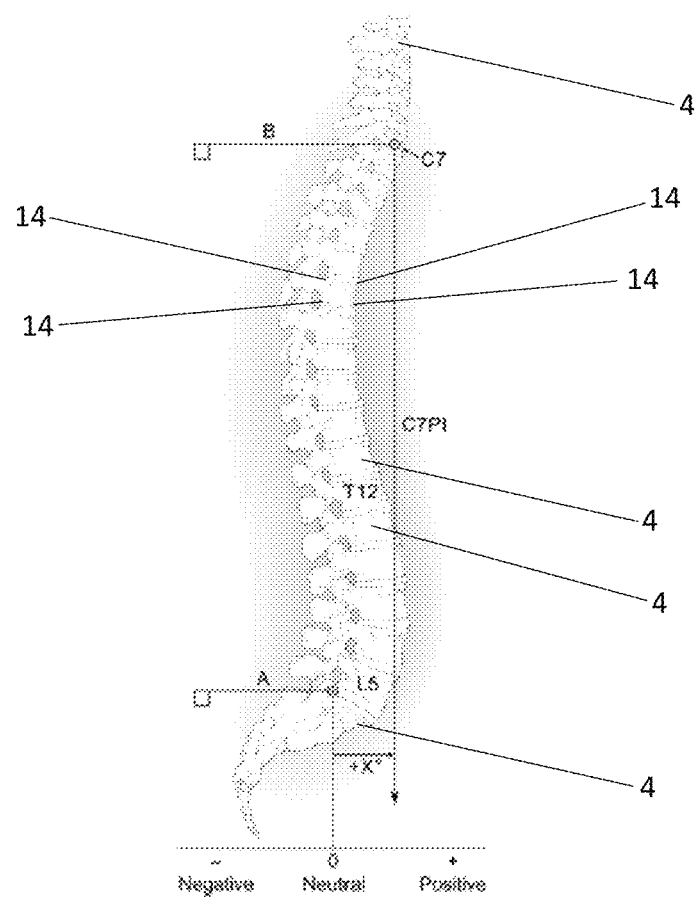
FIG. 1 is a side elevation view of a spine.
Figure 2:
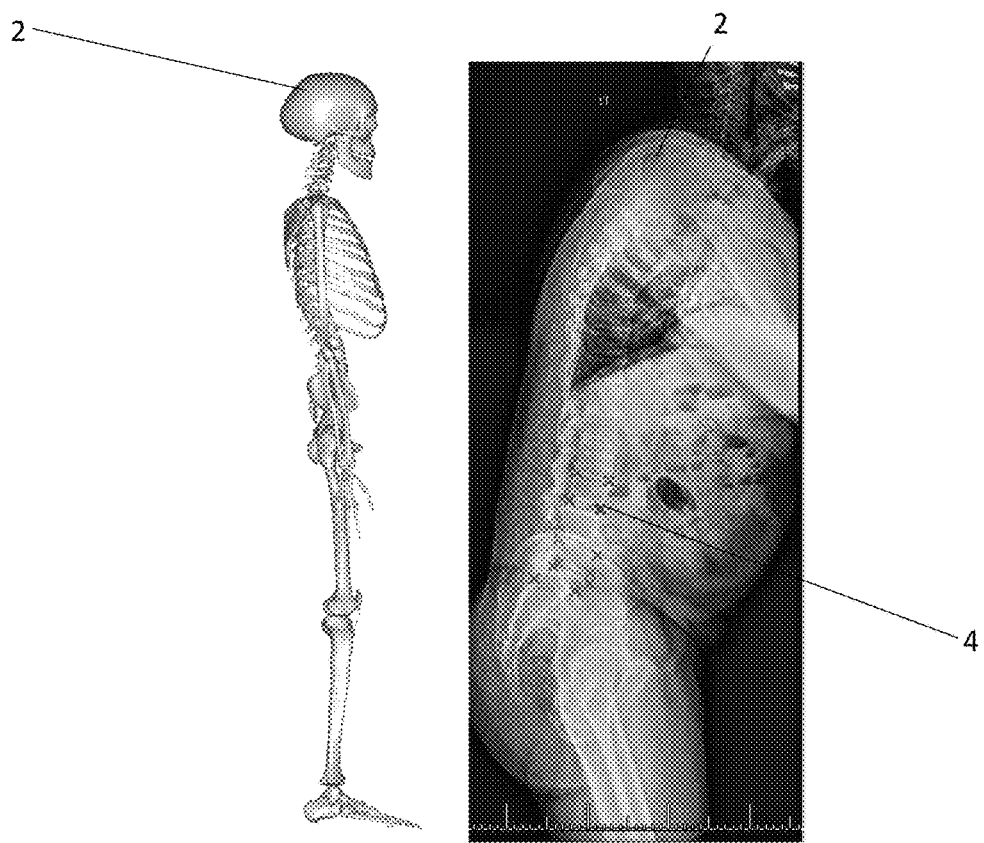
FIG. 2 illustrates a spine of a subject and an X-ray image of a subject.
Figure 8:
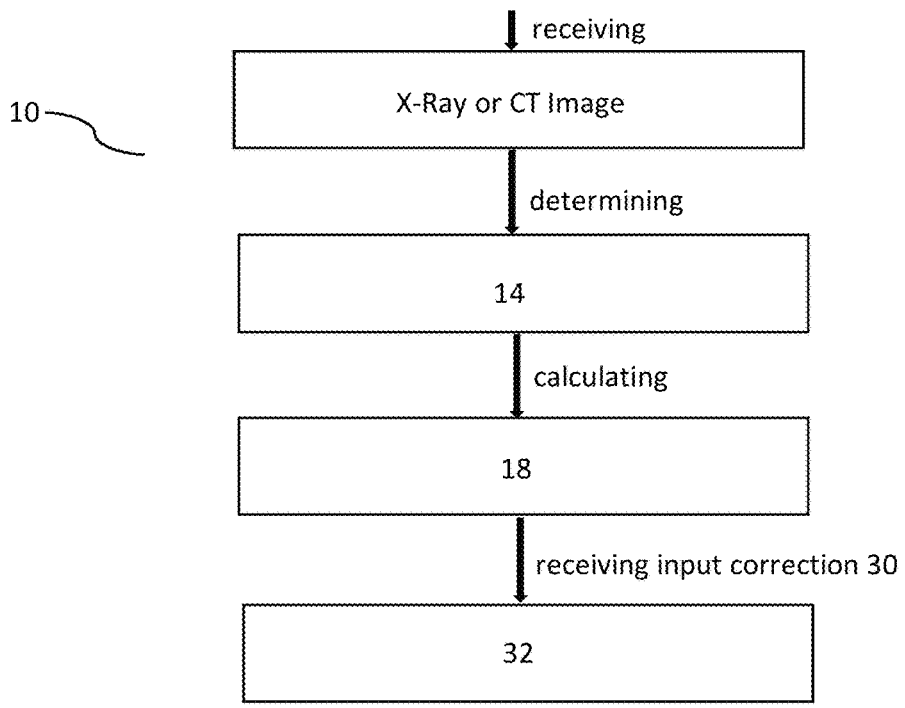
FIG. 8 illustrates steps of generating a musculoskeletal model of a subject according to an embodiment of the system.

In one embodiment, a system 10 for surgical planning and assessment of spinal deformity correction in a subject 2 includes a spinal imaging system 10 capable, or configured, to collect at least one digitized position 14 of one or more vertebral bodies 4 of the subject 2, shown in FIG. 1. It will be appreciated that the present discussion may be applicable to other structures, such as skull bodies and limb joints. The vertebral bodies 4 may be, for example, cervical, thoracic, lumbar, sacrum, or coccyx. The system 12 includes a control unit 16 containing software configured to receive, or collect, the digitized position 14, as shown in, for example, FIG. 8. The at least one digitized position 14 may be any number of positions that correspond to any number of locations, respectively, on the one or more vertebral bodies 4. For example, there may be at least two positions, at least four positions, at least eight positions, at least sixteen positions, or any number of positions therebetween. The at least one digitized position 14 may correspond to specific locations on the one or more vertebral bodies 4. In one embodiment, the positions 14 correspond to a corner, or multiple corners, of the vertebral bodies 4, as shown in FIG. 2. The control unit 16 may also be configured to collect information of the vertebral bodies 4, such as bone density, fractures, etc. The digitized positions 14 may be extracted from the subject 2 when the subject 2 is in a standing, lateral position.

Figure 6:
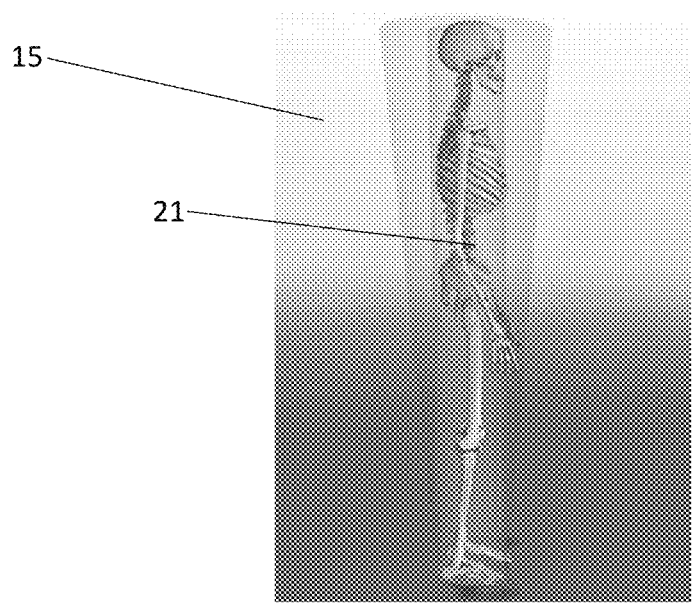
FIG. 6 illustrates a musculoskeletal model in an embodiment of the system.

The control unit 16 may collect the digitized position 14 from any data source of the subject 2 that depicts the vertebral bodies 4 in sufficient detail, including but not limited to, an X-ray image, a computed tomography image, a magnetic resonance imaging image, or biplanar X-ray image of the subject 2. The control unit 16 may contain image recognition software whereby the control unit 16 digitizes data provided, such as an X-ray image, a computed tomography image, a magnetic resonance imaging image, or biplanar X-ray image of the subject 2, and the control unit 16 may select digitized positions 14 based on output from the image recognition software. The image recognition software, by way of example, may process the image and identify and transmit the positions 14, such as the corners of the one or more vertebral bodies 4. In some embodiments, this processing and identification is automatic, while in other embodiments, a user manually selects or verifies the positions 14 from data provided to the control unit 16 such that the control unit 16 receives the digitized positions 14 from the user. In yet another embodiment, the digitized positions 14 are received digitally from a digital imaging component, such as a digital radiography system. The digitized positions 14 may be displayed using medical modeling system 15, such as the archiving and communication system (PACS), shown in FIG. 6.

In an embodiment of the system 10, the control unit 16 is configured to calculate, or determine, based on the at least one digitized position 14, an optimized posture 18 of the subject 2. As used herein, "optimized posture" refers to the posture that would be the desired, or ideal, clinical outcome for the subject 2, as for example, determined by a surgeon seeking to perform a spinal correction surgery on the subject 2 who is in need thereof. The control unit 16 may be configured to calculate the optimized posture 18 by parametric processing. In parametric processing, data regarding the at least one digitized position 14 may be compared to one or more predetermined optimized anatomical posture models 20. The predetermined optimized anatomical posture models 20 may not be patient-specific. The predetermined model 20 selected may be, for example, the predetermined model 20 that most closely corresponds to the anatomical characteristics of the subject 2. By way of example, the control unit 16 may be configured to include, or store, predetermined models 20 for subjects 2 of varying ages, gender and medical conditions (e.g., lordosis, kyphosis, scoliosis), and may select the predetermined model 20 most suitable for the subject 2. The at least one anatomical digitized positions 14 may be morphed, scaled, or adjusted, either manually or automatically, onto corresponding points 21 on the predetermined model 20. As discussed later, the predetermined model 20 may contain logic, inputs, and parameters for the predicting steps when determining optimized posture and/or simulated correction 24.

Figure 9:
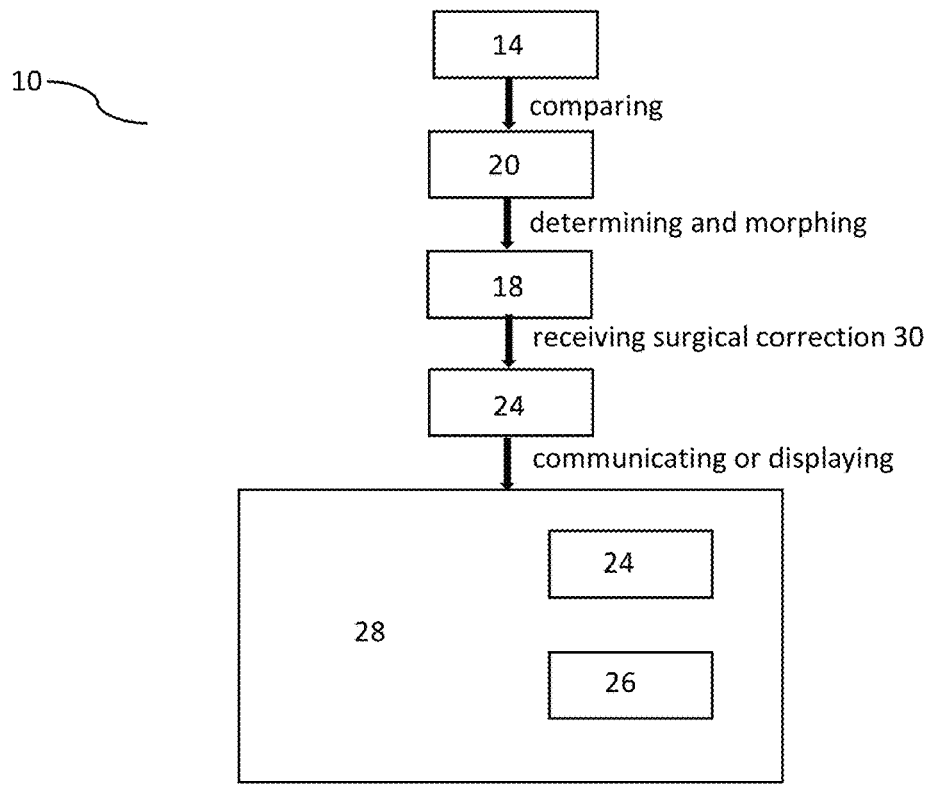
FIG. 9 illustrates steps of generating an output according to one embodiment of the system.

Based on the received at least one digitized position 14 of the one or more vertebral bodies 4, the control unit 16 is configured to predict, or determine, a simulated postoperative surgical correction 24 (i.e., predict how a surgical correction, such as a posterior lumbar interbody fusion or anterior lumbar interbody fusion, will affect the posture of the subject 2). The control unit 16 may be configured to determine, for example, the simulated postoperative surgical correction 24 that would result in, or close to, the optimized posture 18 for the subject 2. Based on the simulated postoperative surgical correction 24, the control unit 16 may be configured to determine, and display to a surgeon, a recommended surgical plan 26 to implement the predicted simulated postoperative surgical correction 24. The recommended surgical plan 26 may include, by way of example, information regarding surgical procedure, surgical approach, surgical technique, surgical instrument, and implant. The control unit 16 may communicate the predicted simulated postoperative spinal correction 24, and/or recommended surgical plan 26, to the user. By way of example and as shown in FIG. 9, the control unit 16 may be configured to communicate, or output, the predicted simulated postoperative surgical correction 24, corresponding to a variance from the calculated optimized posture 18. The communicated predicted simulated postoperative spinal correction 24, and/or recommended surgical plan 26 may be transmitted as an output 28. By way of example, the output 28 may be an image representation, a graphical display, or a numerical value.

Figure 10:
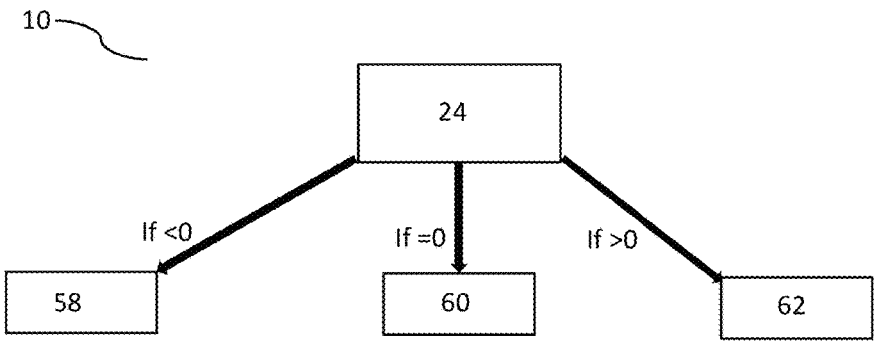
FIG. 10 illustrates steps of displaying results of a simulated surgical correction according to an embodiment of the system.

As illustrated in FIG. 10, in embodiments having output 28 as a numerical value, the output value of less than 0 may represent a predicted undercorrection 58 as compared to the optimized posture 18 and the output value of greater than 0 may represent an overcorrection 62 as compared to the optimized posture 18. A value of 0 may represent a desired, or optimal, spinal correction 60 that achieves the optimized posture 18 in the subject 2. Thus, the value of the output 28 may correspond to the variance of the predicted simulated postoperative surgical correction 24 with the optimized posture 18, with a higher degree positively correlating with higher variance. As used herein, "undercorrection" means that the predicted simulated postoperative surgical correction 24 is not able to fully correct the medical condition being corrected of the subject 2, and "overcorrection" means that that the predicted simulated postoperative surgical correction 24 overly corrects the medical condition being corrected of the subject 2. The value of the output 28 may correspond to any, or any combination, of measurements such as, a value of muscle activation in a patient, a value of kyphosis, a value of lordosis, and a value of Cobb angle.

Figure 11:
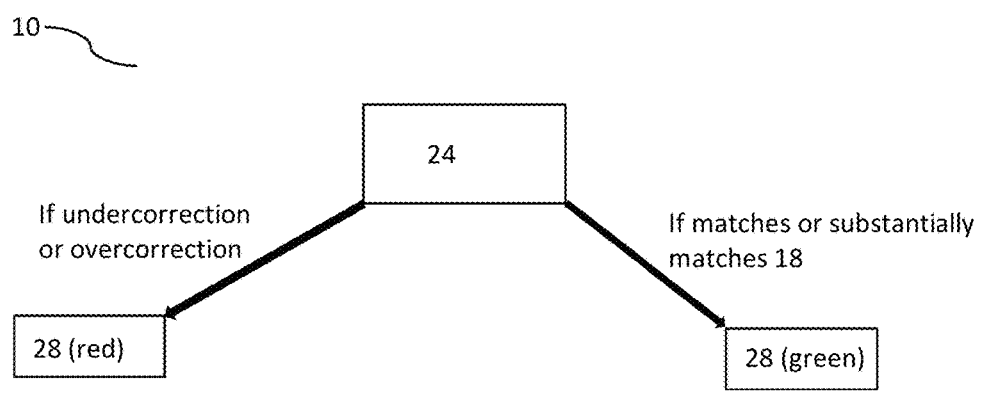
FIG. 11 illustrates steps of displaying results of a simulated surgical correction according to another embodiment of the system.

As described in FIG. 11, if the simulated postoperative surgical correction 24 results in a significant overcorrection or an undercorrection, the system 10 may display the output 28 in red, such as a red number or a red symbol. On the other hand, if the simulated postoperative surgical correction 24 results in an output 28 equal, or substantially equal, to the corresponding value in the optimized posture 18, the system 10 may display an output in green, such as a green number or a green symbol. The control unit 16 may be configured to transmit the outputs 28. Thus, the user (i.e., surgeon) can iteratively change an input plan or input parameters until the goal, such as optimal posture, is achieved.

By way of example, in the case of the subject 2 having Scoliosis, an X-ray image of the subject's 2 spine may be received by the control unit 16. The control unit 16 may automatically process the X-ray image to determine digitized positions 14, such as on points corresponding to corners of vertebrae bodies 4 of the subject 2. Using the digitized positions 14, the control unit 16 may calculate the optimized posture 18 of the subject 2. The control unit 16 may morph and scale the digitized positions 14 onto a predetermined model 20 to create a simulated model 32 of the subject's 2 spine. The optimized posture 18 may have a spine with a Cobb angle of between 0 and 10 degrees, 2 and 8 degrees, or 2 and 6 degrees, or any combination of those values. The Scoliosis subject 2 may have a spinal Cobb of greater than 10 degrees, greater than 15 degrees, greater than 20 degrees, greater than 40 degrees, greater than 50 degrees, or greater than 60 degrees. The control unit 16 may communicate the Cobb value of the optimized posture 18 to the user. The control unit 16 may be configured to receive an input surgical correction 30, such as spinal fusion of specific vertebrae, to calculate the predicted simulated postoperative spinal correction 24, and/or recommended surgical plan 26. In some embodiments of the system 10, multiple plans 26 are recommended. If the optimized posture 18 has a Cobb angle of 0, and the simulated postoperative spinal correction 24 has a Cobb angle of 0, the control unit 16 would communicate to the user that the input surgical correction 30 achieves the optimized posture 18, such as by returning a value of 0. In contrast, if the optimized posture 18 has a Cobb angle of 0, and the simulated postoperative spinal correction 24 has a Cobb angle of −5 or +5, the control unit 16 would communicate to the user that the input surgical correction 30 results in an undercorrection of −5 or overcorrection of +5, respectively. Of course, the values that represent an undercorrection and overcorrection, such as degree and positivity, may be varied. In some embodiments, the control unit 16 may calculate and determine the predicted simulated postoperative surgical correction 24 to achieve the Cobb angle of 0 and determine a recommended surgical plan 26 that would result in the subject 2 having a Cobb angle of 0. The control unit 16 may be configured to communicate the simulated correction 24 and/or plan 26 to the user.

As can be appreciated, the system 10 may have numerous advantages. For example, the system 10 may provide the user with the optimized posture 18 of the subject 2. Using the optimized posture 18, the user may determine the optimal surgical plan 26 to achieve the optimized posture of the subject 2. In embodiments of the system 10 where the control unit 16 is configured to receive an input surgical correction 30 and output a simulated correction 24, the system 10 enables the user to remove the uncertainty, or "guesswork," as to the clinical outcome of a surgical correction. Advantageously, this feature of the system 10 would provide the user with information, such as whether the proposed surgical correction would result in an undercorrection of the medical condition being treated, that would allow the user to choose the surgical correction that would result in an efficacious clinical outcome for the subject 2 that avoids undercorrection or overcorrection. In embodiments where the system 10 predicts optimal correction 24 and/or plan 26 and communicates correction 24 and/or plan 26 to the user, the system 10 provides the user with an efficacious surgical correction that a surgeon can implement that avoids undercorrection or overcorrection. Indeed, the described system 10 is a new technological tool for improving surgical outcomes in subjects 2, particularly human subjects in need of and who receive spinal correction surgery.

Figure 3:
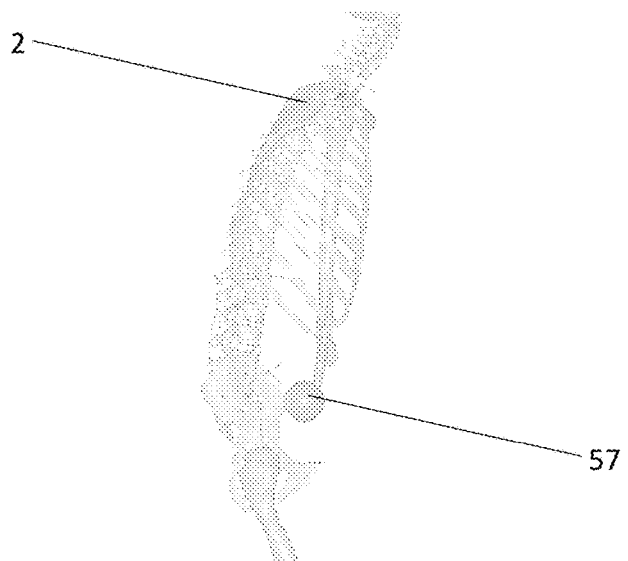
FIG. 3 illustrates a spine of a subject.
Figures 5A, 5B:
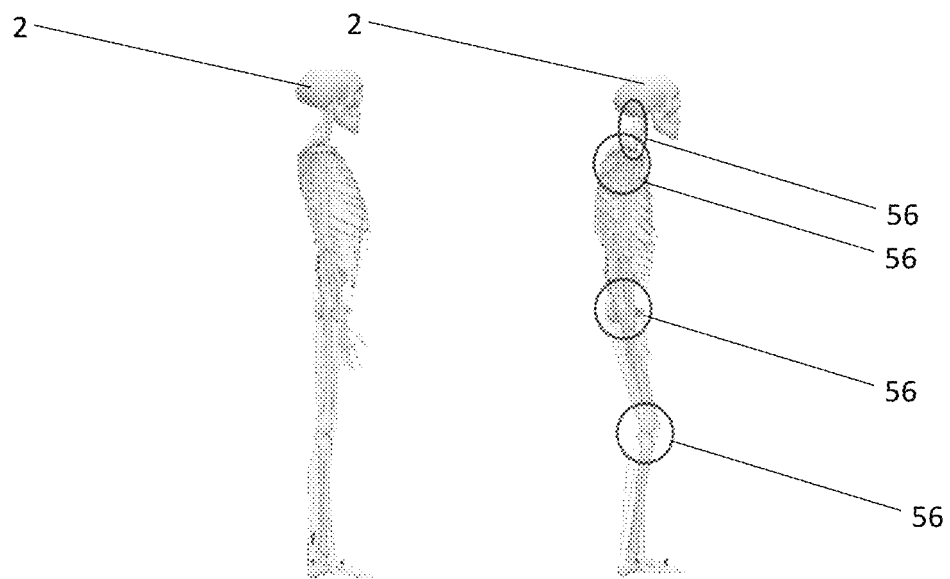
FIGS. 5A and 5B illustrate a model of a healthy spine and a kyphotic spine, respectively.

The control unit 16 is configured to process various values and factors, as well as contain various logics, to calculate optimized posture 18 and simulated postoperative surgical correction 24. For example, the control unit 16 may be configured to receive and process one or more compensation values 56 selected from the group consisting of: knee flexion, pelvic movement, ankle flexion, shoulder movement, lumbar movement, thoracic movement, cervical movement, spinal compensation, including ribs and neck, and a combination thereof, as shown in FIG. 5B. The control unit 16 may also be configured to receive and process center of mass migration 57. Knee flexion refers to joint angle between the bones of the limb at the knee joint. Knee flexion values may be, for example, between minus 10 and 150 degrees. Pelvic movement may include pelvic retroversion, pelvic anteversion, and pelvic tilt. Pelvic retroversion may be, for example, less than 50 degrees, less than 30 degrees, less than 25 degrees, less than 20 degrees, less than 15 degrees, less than 10 degrees, less than 5 degrees, or any range thereof. Center of mass migration 57, as shown in FIG. 3, refers to the point on the ground over which the mass of the subject 2 is centered, typically the center of mass migrations falls between the ankles of the subject 2. Ankle flexion refers to a joint angle between the bones of the limb at the ankle joint. These values may be taken from the subject 2 who is in a suitable position, such as standing, supine, and prone. Processing compensation values 56 and mass migration 57 is a technical problem much more difficult than that of processing a rigid skeleton with no compensation (FIG. 5A) that is overcome by the practicing of the present disclosure.

Figures 4A, 4B, 4C:
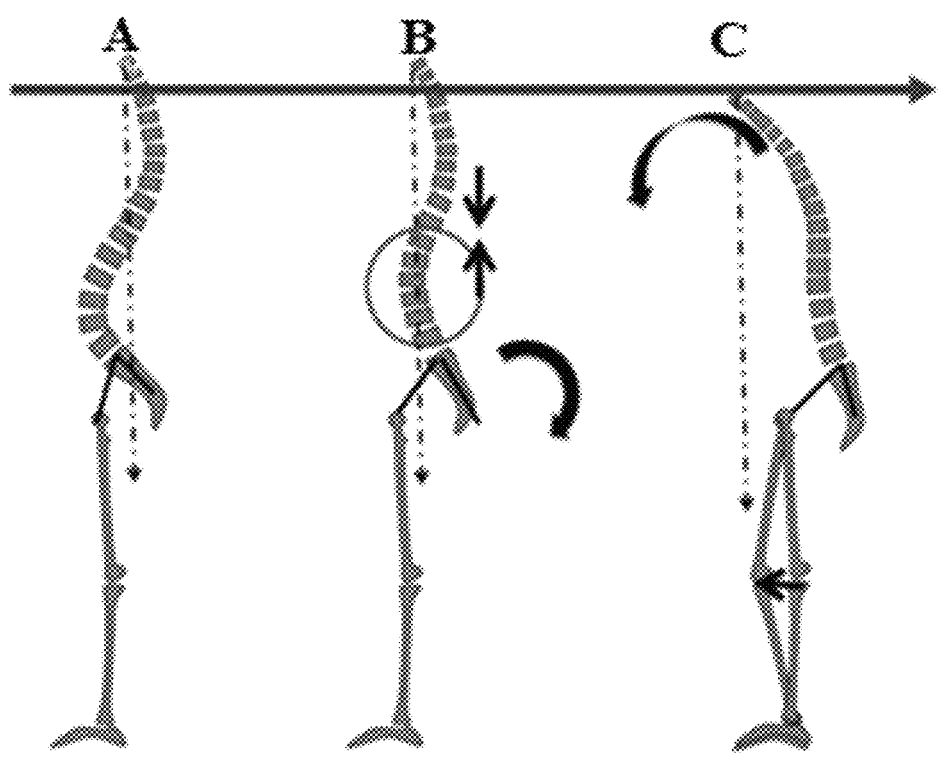
FIGS. 4A-4C illustrate various configurations of a spine.

FIG. 4A illustrates a non-degenerated spine with the spine in balance. FIG. 4B illustrates a generated spine and retroversion of the pelvis to compensate for the degeneration. FIG. 1C depicts a generated spine and flexion of the knee to compensate for such degeneration. Beneficially, the disclosed system and methods herein can account for these compensations, among other things, to produce a realistic and accurate model for surgical planning.

Figure 12:
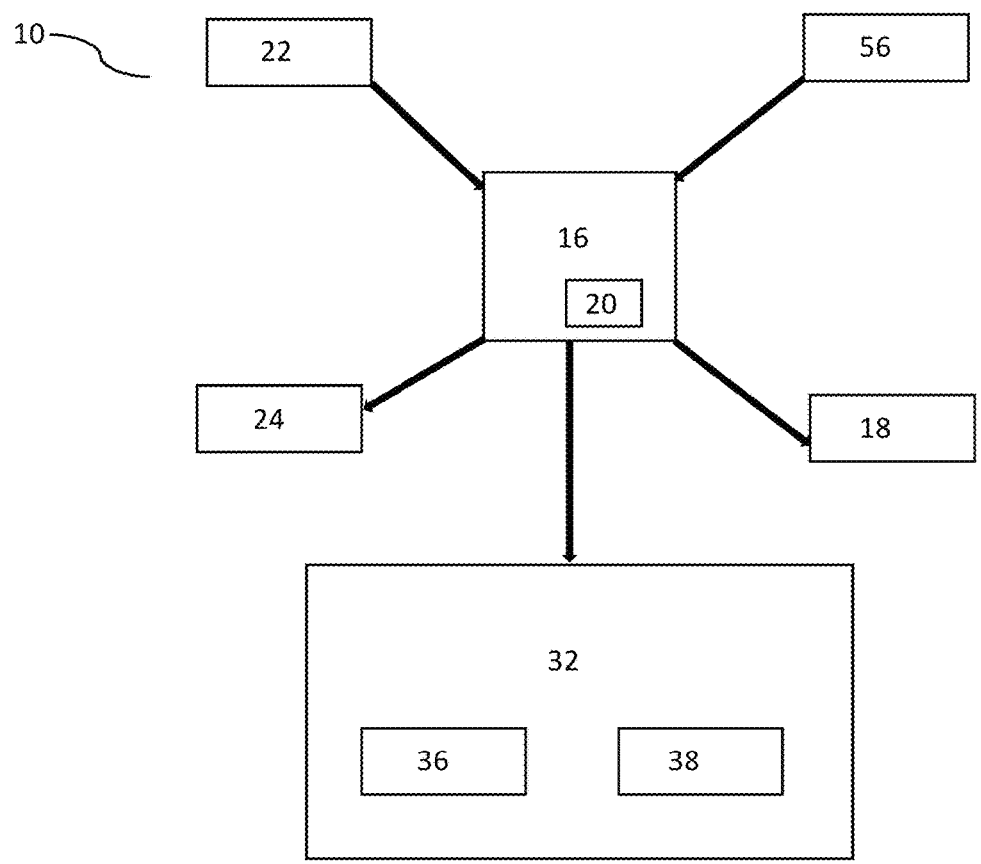
FIG. 12 illustrates an embodiment of the system.

As shown in FIG. 12, the control unit 16 may be configured to generate, or create, a musculoskeletal model 32 of the subject 2. The control unit 16 may be configured to compare the model 32 with the predetermined model 20 for the control unit's 16 calculation of the optimized posture 18. The control unit 16 may receive the digitized positions 14 to generate the musculoskeletal model 32 of the subject 2. The control unit 16 may also receive inputs 22, such as spinopelvic parameters, ligament parameters, joint kinematics, sagittal alignment measurements, spinal instability, and muscle recruitment criteria, and intervertebral fusion. As shown in FIGS. 7A-7C, the spinopelvic parameters may include parameters such as pelvic tilt (PT), sacral slope (SS), pelvic incidence (PI), sagittal vertical axis (SVA), lumbar lordosis, thoracic kyphosis, T1 pelvic angle, and combinations thereof. Further, the control unit 16 may input or use global alignment parameters such as global sagittal axis, three-dimensional parameters such as rotation and scoliosis, and cervical parameters. In some embodiments of the system 10, the spinopelvic parameters are used to assess, or determine, how far a subject is from a normal or optimum posture. The model 32 may also include muscle 36 force data or muscle activation data 38. The control unit 16 may be configured to use the inputs 22 to generate the musculoskeletal model 32 of the subject 2 and optimized posture 18 of the subject 2, which can include any, or all, of these parameters and inputs that reflect their respective values, or age-adjusted respective values, on the model 32. The control unit 16 may be configured to receive these inputs 22 manually or automatically. The control unit 16 may use these inputs 22 to compare and process in comparison to corresponding values on a predetermined model 20 in calculating optimized posture 18 and simulated surgical correction 24. Models 20, 32 may each have, or exclude, any parameter, logic, algorithm, input, or output discussed herein.

Figure 15:
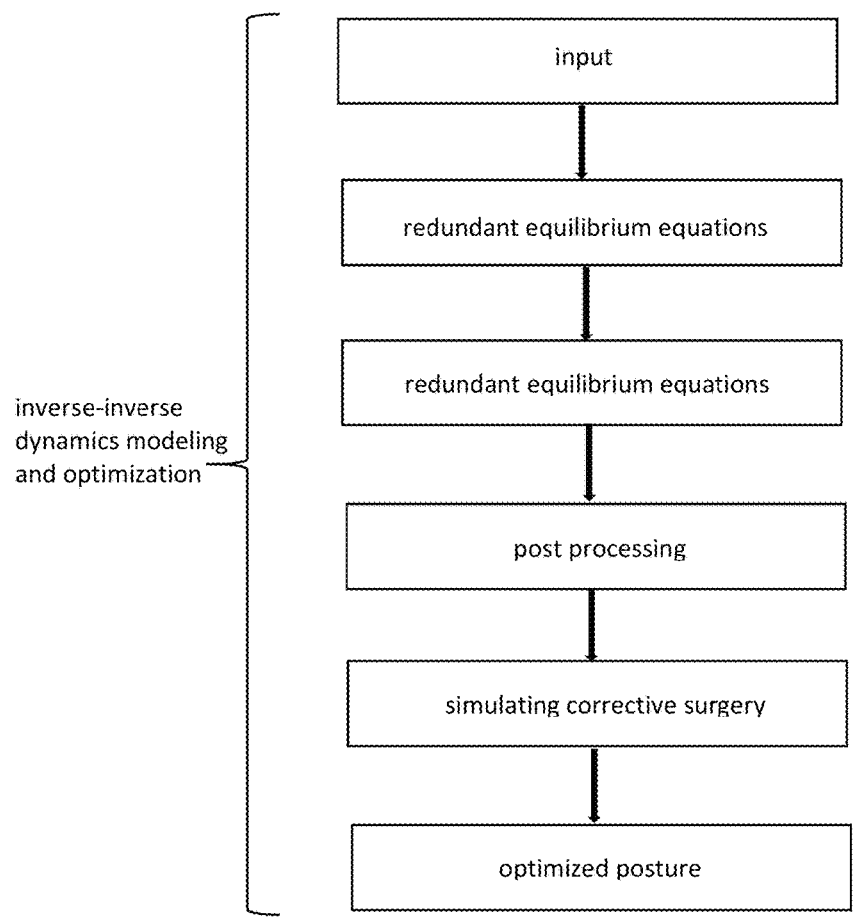
FIG. 15 illustrates steps of inverse-inverse dynamics processing and optimization according to an embodiment of the system.

The control unit 16 may process the digitized positions 14 by inverse-inverse dynamics modeling (FIG. 15). Advantageously, inverse-inverse dynamics modeling enables the system 10 to create a fluid model as opposed to a rigid model. Indeed, inverse-inverse dynamics modeling solves the technical problem of simulating how fluid joints and connectors (e.g., inputs 22) of subjects 2 affect a corrective surgery, particularly in instances where a rigid model would generate a model that would result in an undercorrection if implemented in a surgical correction. The control unit 16 may contain anatomical modeling software capable of, or configured to, simulate kinematics and muscular and joint loads in the full body for typical activities of a subject 2 and for fundamental human body motions. An example of such software is ANYBODY MODELING SYSTEM™ software, available from ANYBODY TECHNOLOGY™ of Aalborg, Denmark, configured to execute the inverse-inverse dynamics modeling. Moreover, the inverse-inverse dynamics model improves the functioning of control unit 16, as inverse-inverse dynamics enables control unit 16 to more accurately simulate the simulated surgical correction's interactions with anatomical properties of subject 2, especially properties specific to that subject 2, such as compensation, muscle elasticity, and joint elasticity.

Figure 13:
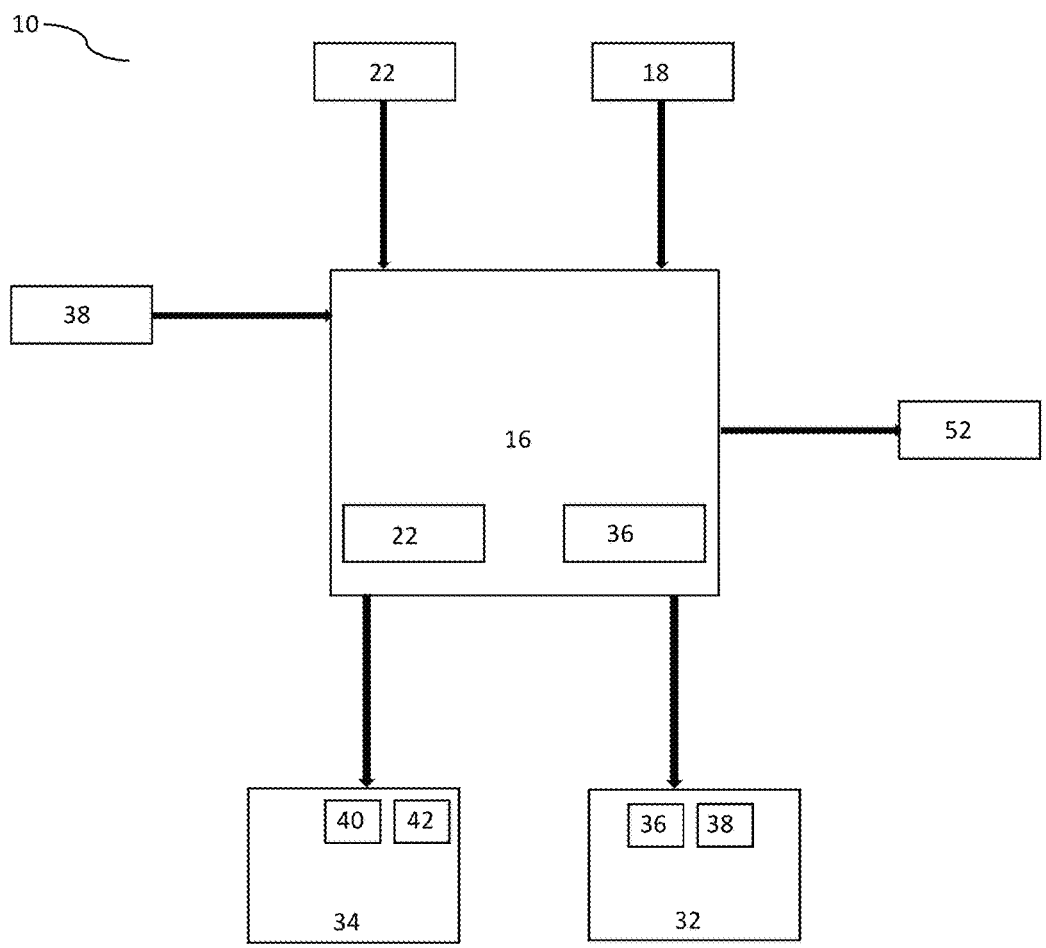
FIG. 13 illustrates yet another embodiment of the system.

As illustrated in FIG. 13, the control unit 16 may be configured to generate a sagittal curvature profile 34 based on the received digitized positions 14 and inputs 22. The profile 34 may be both a sagittal and coronal. The control unit 16 may morph (i.e., modify) the model 32 to match the profile 34. The musculoskeletal model data may be modified by scaling, adjusting positioning of the one or more vertebral bodies 4, morphing the simulated subject anatomical model 32, or combinations thereof.

Some, or all, of the inputs 22 may be predetermined, or manually or automatically received. The control unit 16 may be configured to apply logic parameters 36, such as that a subject 2 maintains a center of mass over the ankles; maintains a constant horizontal gaze; stands in a posture where postural muscle energy is minimized; has an arm position matching the patient during imaging (i.e., scaling); has no coronal plane deformity, or any combination of these logic parameters 36.

The control unit 16 may be configured to compare the calculated, or generated, musculoskeletal model 32 with predetermined musculoskeletal model data levels. Data from the calculated musculoskeletal model 32, such as muscle force data 36 or muscle activation data 38, may be used to calculate the simulated surgical correction 24 and communicated to a user through a display 52.

The control unit 16 may receive and process compensation values 56. In some embodiments, these values may be stored on the control unit 16. The control unit 16 may calculate compensation data 38, for example, hip compensation, ankle joint compensation, knee joint compensation, shoulder compensation, lumbar compensation, thoracic compensation, cervical compensation, or spinal compensation, including ribs and neck, to generate the model 32. Including compensation values 56 and/or compensation data 38 is particularly useful in some embodiments of the system 10, as the compensation values 56 and compensation data 38 considers that joints compensate for spinal changes, such as a degenerated spine. Thus, by including the values and data 56, 38, model 32 may be more accurately the subject's anatomy and compensation. The control unit 16 may also store predetermined compensation data 38 that is associated with the predetermined model 20.

The control unit 16 may also be configured to include a prediction of trunk muscle force 40 output and leg muscle force output 42 in the prediction of the simulated postoperative surgical correction 24. The trunk muscle force output may include cervical output, an erector spinae output, multifidi output, an obliques output, semispinalis output, an abdominal muscles output, or any combination thereof. The leg muscle force output includes a soleus output, a gastrocnemius output, a hip and knee flexors output, a hip and knee extensors output, a gluteus maximus output, a gluteus minimus output, or any combination thereof. These outputs 42, 44 may be communicated to a user through the display 52.

Figure 14A:
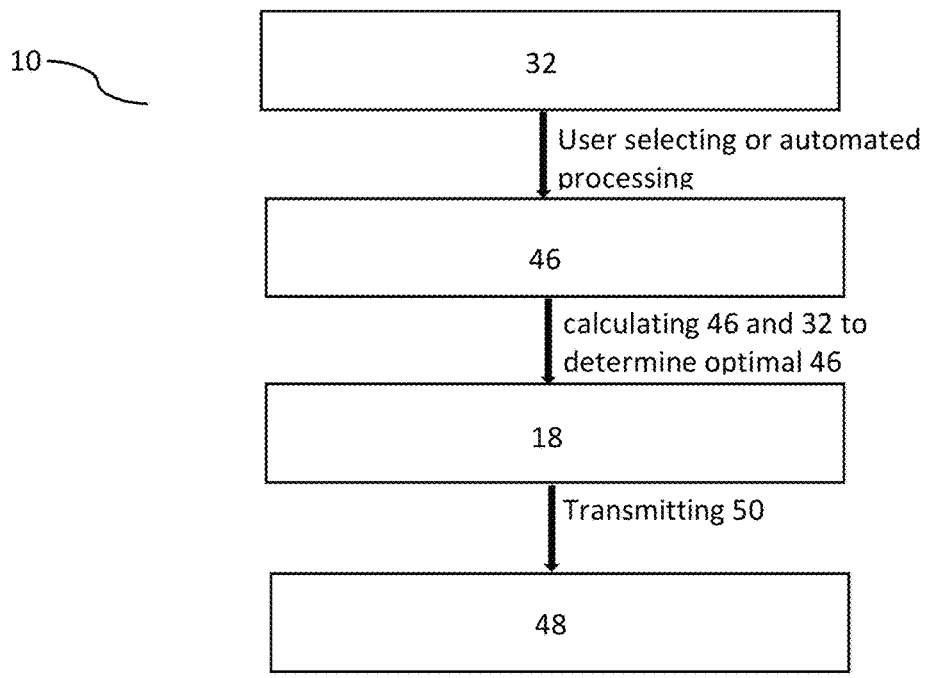
FIG. 14A illustrates steps for transmitting simulated implant data to an additive or subtractive manufacturing device according to an embodiment of the system.
Figure 16:
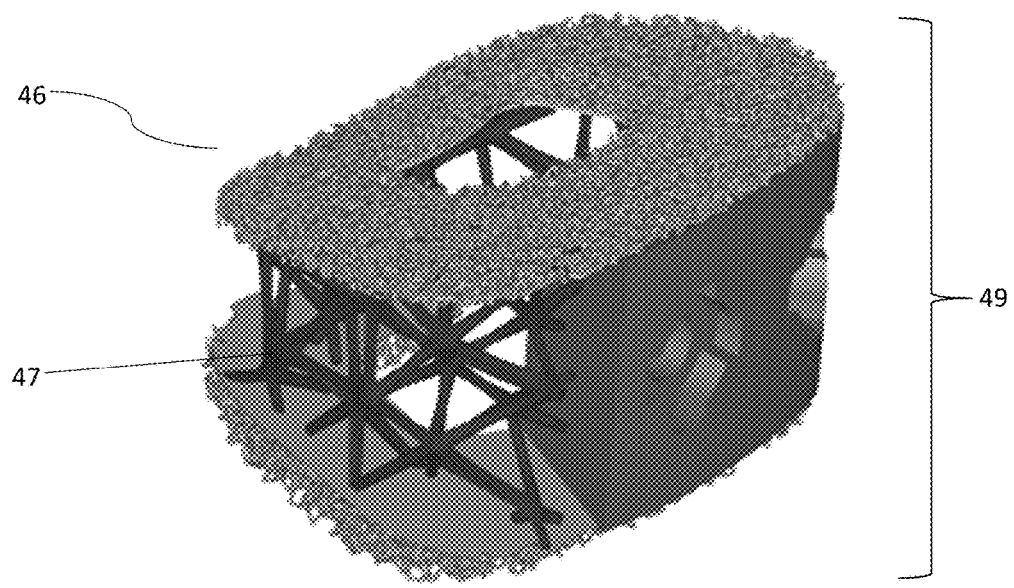
FIG. 16 illustrates a simulated implant according to an embodiment of the system.

As shown in FIG. 14A, in some embodiments of the system 10, the simulation of the postoperative surgical correction 24 includes simulating an implant 46 (FIG. 16) in the simulated model 32 of the subject 2. For example, a user of the system 10 may select, or design using engineering software, a simulated implant 46 to use in conjunction with the simulated postoperative surgical correction 24. The control unit 16 may be configured to receive input from the user for the location, orientation, type, size, and profile of the implant 46. In some embodiments of the system 10, the control unit 16 is configured to determine the simulated implant 46 that would achieve optimal posture 18 in the simulated corrective surgery 24. The determination may include the dimensions, location, orientation, type, size, and profile of the implant 46.

Figure 14B:
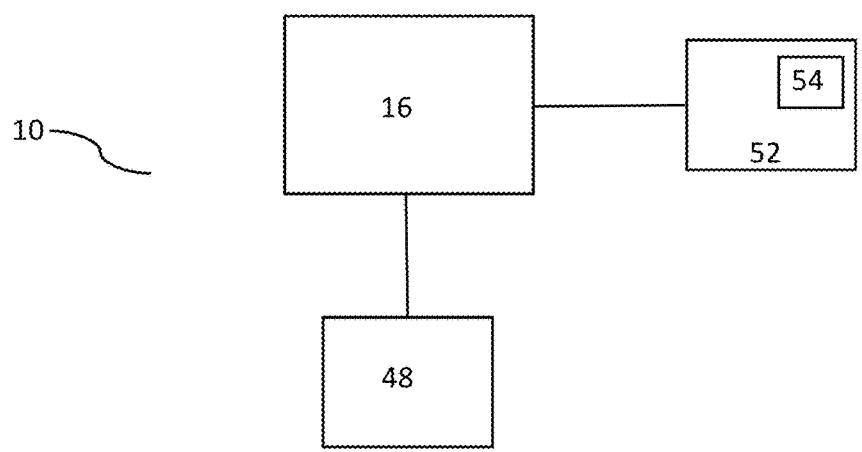
FIG. 14B illustrates an embodiment of the system having an additive or subtractive manufacturing device.

As illustrated in FIG. 14B, the system 10 may include a three dimensional printer (i.e., an additive manufacturing device or a subtractive manufacturing device) 48 in communication with the control unit 16. The three dimensional printer 48 may be configured to create, or partially create, the determined implant 46. Advantageously, this feature of the described disclosure allows for personalized surgical implants that are optimized for clinical benefit in the subject 2 to achieve optimized posture 18. The control unit 16 may be configured to transmit digital data 50 about the implant 46 for the printer 48 to manufacture the implant 46. The implant 46 may be designed on design software executed by the control unit 16 to achieve a desired structure and exported, for example as a .STL file, for preparation to be built with the three dimensional printer 48. The implant 46 may be designed to have a profile 49 to custom fit the morphology of vertebral body endplates of the subject 2, which may vary from subject to subject. The implant manufactured from simulated implant 46 may be constructed of any number, including multiple, suitable biocompatible material, such as titanium, titanium-alloy or stainless steel, surgical steel, or non-metallic compounds such as polymers.

In another aspect, a system 10 for surgical planning and assessment of spinal deformity correction in a subject 2 includes a spinal imaging device capable of collecting and transmitting to a control unit 16 at least one digitized position 14 of one or more vertebral bodies 4 of the subject 2. The control unit 16 is may be configured to receive the at least one digitized position 14 of the one or more vertebral bodies 4 of the subject 2, and calculate, based on morphing and scaling the at least one digitized position 14 onto a predetermined model 20 to form a simulated model 32, an optimized posture 18 for the subject 2.

The control unit 16 may be configured to execute software including optimization algorithms that tailor the profile of the implant 46 based upon loading conditions imparted upon the implant 46, including: compression, shear, and torsion. The control unit 16 may include optimization algorithms that may be executed in order to produce a low-density, material efficient implant 46. This is accomplished by applying multiple, clinically-relevant, loading conditions to the implant 46 in the software program and allowing a finite element solver to optimize and refine, for example, a body lattice structure 47 of the implant 46.

The system 10 may include a display 52, such as a monitor, in communication with the control unit 16. The display 52 may be capable of receiving input from the user in addition to communicating feedback information to the user. By way of example (though it is not a necessity), a graphical user interface 54 (GUI) is utilized to enter data directly from the screen display 52.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

The following is claimed:

1. A system for surgical planning and assessment of spinal deformity correction in a subject, the system comprising:
    a spinal imaging system capable of collecting at least one digitized position of one or more vertebral bodies of the subject;
    a control unit in communication with the spinal imaging system, said control unit being configured to:
        (a) determine a model of the subject based on the at least one digitized position of the one or more vertebral bodies received from the spinal imaging system, wherein the at least one digitized position of the one or more vertebral bodies corresponds to a standing lateral position of the subject;
        (b) calculate an optimized posture for the subject based on a comparison of the determined model and one or more predetermined models that correspond to one or more anatomical characteristics of the subject;
        (c) receive one or more simulated spinal correction inputs, wherein the one or more simulated spinal correction inputs comprise one or more of (i) muscle force data and (ii) muscle activation data;
        (d) predict a simulated postoperative surgical correction that maintains a center of mass over the ankles of the subject based on the received one or more simulated spinal correction inputs and the calculated optimized posture for the subject; and
        (e) determine a surgical plan based on the predicted simulated postoperative surgical correction and communicate the determined surgical plan via a display.

2. The system of claim 1, wherein the digitized position is on at least one of the corners of the one or more vertebral bodies.

3. The system of claim 1, wherein the one or more vertebral bodies includes two or more vertebral bodies.

4. The system of claim 1, wherein the control unit is further configured to
    (f) communicate the predicted simulated postoperative spinal correction to a user.

5. The system of claim 1, wherein the at least one digitized position of the one or more vertebral bodies are obtained from X-ray data, computed tomography data, magnetic resonance imaging data, or biplanar X-ray data from the subject.

6. The system of claim 1, wherein the at least one digitized position is processed to generate a musculoskeletal model of the subject.

7. The system of claim 6, wherein the musculoskeletal model processing comprises inverse-inverse dynamics modeling.

8. The system of claim 6, wherein the musculoskeletal model includes spinopelvic parameters, ligament parameters, joint kinematics, or any combination thereof.

9. The system of claim 6, wherein the control unit is further configured to
    (f) compare the generated musculoskeletal model with predetermined musculoskeletal model data levels.

10. The system of claim 6, wherein the control unit is further configured to
    (f) generate a sagittal curvature profile based on the received at least one digitized position of the one or more vertebral bodies.

11. The system of claim 10, wherein the control unit is further configured to
    (g) modify the musculoskeletal model to match the sagittal curvature profile.

12. The system of claim 11, wherein the modifying of the musculoskeletal model comprises scaling, adjusting positioning of the one or more vertebral bodies, morphing a simulated subject anatomy, or combinations thereof.

13. The system of claim 1, wherein the prediction of the simulated postoperative surgical correction comprises a prediction of simulated anterior lumbar interbody fusion surgery.

14. The system of claim 1, wherein the prediction of simulated postoperative surgical correction is based on one or more values selected from the group consisting of: knee flexion, ankle flexion, pelvic retroversion, spinal compensation, and a combination thereof.

15. The system of claim 1, wherein the one or more simulated spinal correction inputs includes sagittal alignment, muscle recruitment criteria, or a surgical procedure.

16. The system of claim 1, wherein the simulated postoperative surgical correction includes hip compensation, knee joint compensation, or ankle joint compensation.

17. The system of claim 1, wherein the control unit is further configured to
(f) output a value, based on the predicted simulated postoperative surgical correction, corresponding to a variance from the calculated optimized posture.

18. The system of claim 1, wherein the simulated postoperative surgical correction comprises simulating an implant in the subject.

19. A system for surgical planning and assessment of spinal deformity correction in a subject, the system comprising:
a spinal imaging system capable of collecting at least one digitized position of one or more vertebral bodies of the subject; and
a control unit in communication with the spinal imaging system, said control unit being configured to:
(a) determine a model of the subject based on the at least one digitized position of the one or more vertebral bodies of the subject received from the spinal imaging system, wherein the at least one digitized position of the one or more vertebral bodies corresponds to a standing lateral position of the subject;
(b) calculate, based on morphing and scaling the determined model of the subject onto a model that includes one or more of (i) muscle force data and (ii) muscle activation data, an optimized posture for the subject;
(c) predict a simulated postoperative surgical correction that maintains a constant horizontal gaze based on the calculated optimized posture for the subject; and
(d) determine a surgical plan based on the predicted simulated postoperative surgical correction and communicate the determined surgical plan via a display.

* * * * *